US005425742A

United States Patent [19]

Joy

[11] Patent Number: 5,425,742

[45] Date of Patent: Jun. 20, 1995

[54] USE OF HOLLOW HYPOBARIC CHAMBERS ON BODY PARTS FOR INCREASING BLOOD FLOW, REDUCING PRESSURE AND DECREASING PAIN

[75] Inventor: Franklin W. Joy, Texas City, Tex.

[73] Assignee: Patrick S. Quigley, Galveston, Tex.

[21] Appl. No.: 218,896

[22] Filed: Mar. 28, 1994

[51] Int. Cl.[6] .......... A61B 17/00

[52] U.S. Cl. .......... 606/203; 601/152

[58] Field of Search .......... 606/201-207; 601/152; 128/898

[56] References Cited

U.S. PATENT DOCUMENTS

| | | | |
|---|---|---|---|
| 26,953 | 12/1902 | Lütje . | |
| 3,807,396 | 4/1974 | Fischel . | |
| 3,878,839 | 4/1975 | Norton et al. | 601/152 |
| 4,343,302 | 8/1982 | Dillon | 601/152 |
| 4,738,249 | 4/1988 | Linman et al. | 606/203 |
| 4,770,170 | 9/1988 | Sato et al. . | |
| 4,825,862 | 5/1989 | Sato et al. . | |
| 4,959,047 | 9/1990 | Tripp, Jr. . | |
| 5,000,164 | 3/1990 | Cooper . | |
| 5,101,819 | 4/1992 | Lane . | |

FOREIGN PATENT DOCUMENTS

| | | | |
|---|---|---|---|
| 0047811 | 11/1978 | U.S.S.R. | 601/152 |

OTHER PUBLICATIONS

Galveston County, "New device heals burns and wounds, makers say", The Associated Press, Sat. Dec. 25, 1993, *The Daily News*, p. 3-A.

*Primary Examiner*—Stephen C. Pellegrino
*Assistant Examiner*—William W. Lewis
*Attorney, Agent, or Firm*—Michael B. Jolly

[57] ABSTRACT

The present invention provides an apparatus and method for subjecting a body part to a vacuum, engorging blood veins and reducing neurophatic pain. The body part is inserted through a donut like inflatable seal which is attached to an opening in the cylindrical rigid hypobaric chamber. The seal is inflated and the chamber evacuated utilizing a single air pump. The seal pressure and chamber vacuum are controlled and adjusted using preset or adjustable pressure release valves.

11 Claims, 3 Drawing Sheets

USE OF HOLLOW HYPOBARIC CHAMBERS ON BODY PARTS FOR INCREASING BLOOD FLOW, REDUCING PRESSURE AND DECREASING PAIN

BACKGROUND OF THE INVENTION

1. Field of the Invention

This invention relates to a device for increasing blood flow in, reducing pressure around and decreasing pain in a body part by surrounding the body part with a hollow hypobaric chamber.

2. Description of the Prior Art

Many patients, particularly diabetic patients, tend to suffer from poor blood flow and neuropathic pain. An insufficient amount of insulin in the body and an excessive amount of sugar in the blood leads to neuropathic pain in body parts of diabetic patients. In order to reduce pain in body parts, diabetics and other groups of patients who suffer from pain due to poor blood flow need increased blood flow in their body parts.

Prior art methods of alleviating pain associated with diabetes comprise medication, exercise and dieting. However, these methods may show limited results and value in reducing neuropathic pain.

In addition, there are a wide variety of prior art devices designed to assist blood circulation. Examples of such prior art devices include: U.S. Pat. No. 5,000,164 issued to Cooper on Mar. 19, 1991, which discloses a circulation enhancing apparatus comprising an airtight boot contoured to fit the injured human foot along with a modulator for providing cyclic over-pressure and vacuum pulses to the boot in synchronism with the heart's systolic and diastolic pressure pulsations; U.S. Pat. No. 4,959,047 issued to Tripp on Sep. 25, 1990, which discloses a flexible lower body negative pressure anti-G suit for protecting against the adverse effects of +G(z-axis) acceleration.

While the devices of the prior art are designed to provide for negative pressure chambers, the prior art devices do not reduce neuropathic pains associated with diabetes.

SUMMARY OF THE INVENTION

It is an object of the present invention to provide a device for reducing pressure around a body part by surrounding the body part with a hypobaric chamber, causing increased blood flow in and decreasing pain, particularly neuropathic pain, of the body part.

It is also an object of the invention to achieve the foregoing object with a relatively simple and relatively inexpensive device.

The invention provides a method for reducing pressure around the body part by surrounding the body part with a hollow hypobaric chamber. Also, the invention preferably provides a method of increasing blood flow and decreasing pain, comprising neuropathic pain associated with diabetes. The unique discovery of the present invention is that surrounding a body part with a hollow hypobaric chamber preferably decreases pressures on that body part and thus stimulates blood circulation to and reduces pain of the body part. The chamber is preferably sized and shaped such that the body part is inserted through an inlet outlet port existing amidst a donut-like inflatable seal attached to a pair of proximate endings located at an interruption in the chamber's perimeter. In a preferred embodiment, the chamber is cylindrical in shape.

The chamber preferably comprises chamber walls which have an inner surface, an outer surface adjacent to a surrounding atmosphere, a perimeter with a first interruption and a second interruption, a first and a second pair of proximate endings located next to the first and the second interruption in the perimeter, respectively. In a preferred embodiment, the first interruption may be located on a first side of the chamber such that an inlet outlet port is created between the first pair of proximate endings on the first side of the chamber. The inlet outlet port on the first side of the chamber most preferably serves as an entry and an exit for the body part under treatment. Preferably, the second interruption may be located on a-second side of the chamber adjacent to the first side between a second pair of proximate endings. The second pair of proximate endings most preferably serves as a connection between the chamber and the surrounding atmosphere.

Also, the invention most preferably is directed to a means for inhibiting the flow of gas comprising air in or out of the chamber adjacent to the surface of the body part. Most preferably, such means for inhibiting the flow of gas in or out of the chamber comprises a donut-like inflatable seal. The seal may be most preferably attached to the first pair of proximate endings on the first side of the chamber. The inflatable seal may be preferably located between the first pair of proximate endings on the first side of the chamber and may be preferably donut-like in shape, with a hole amidst the seal, such that when the body part is inserted into the chamber and the seal is inflated, the seal inhibits gas flow adjacent to the surface of the body part in or out of the chamber.

Preferably, the invention is additionally directed to a means for adjusting pressure in the chamber by withdrawing gas comprising air from the airtight chamber to create a hypobaric chamber. The means for adjusting pressure in the chamber most preferably comprises a first pipe extending between a pump and the chamber, and a first pressure relief valve for adjusting the flow of gas between the pump and the chamber. The second interruption may be preferably located near the bottom of the second side of the chamber as an outlet for connecting the pump. Preferably, air may be withdrawn through the first pipe from the chamber and relieved through adjustments made on the first pressure relief valve into the surrounding atmosphere.

The invention is preferably further directed to a means for adjusting volume and pressure in the inflatable seal. Such means for adjusting volume and pressure in the seal most preferably comprises a second pipe extending from the pump to the inflatable seal, and a second pressure relief valve for adjusting the flow of gas comprising air between the pump and the inflatable seal. The gas may be most preferably supplied by the pump to the inflatable seal to an extent that the inflatable seal fits tightly against the body part and such that gas may be withdrawn from the inflatable seal through adjustments made on the second pressure relief valve. The body part of a patient may be preferably positioned within the hollow chamber such that the inflatable seal sealingly contacts the body part in order to form a seal upon being inflated.

After inflating the seal, a preferred embodiment may be a hypobaric chamber created by closing the first pressure relief valve upon pumping out sufficient gas from the chamber as required for purposes of treatment through using the means for adjusting pressure in the chamber. A person suffering from pain due to poor blood flow, comprising a diabetic, places the body part through the hole amidst the seal. The seal is then inflated to form an airtight seal around the body part. The pump is connected to the outlet of the chamber and the gas is pumped out of the chamber reducing pressure around, increasing blood circulation of and relieving pain, comprising neuropathic pain, of the body part.

BRIEF DESCRIPTION OF THE DRAWINGS

The present invention may be more clearly understood from a reading of the following detailed description in conjunction with the accompanying drawings wherein.

DETAILED DESCRIPTION

Figure 1:
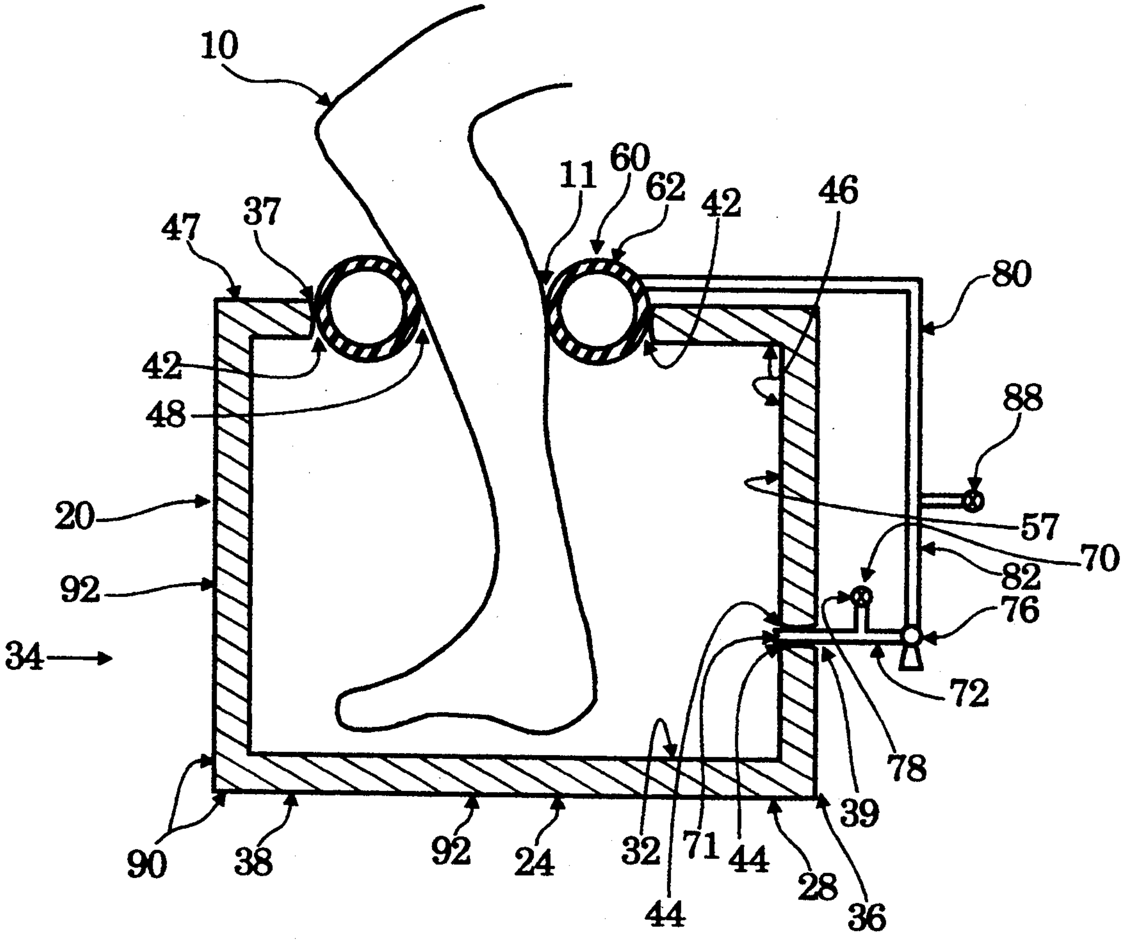
FIG. 1 is a simplified side-view of a leg to which the device for reducing surrounding pressure, constructed according to the teachings of the present invention, has been applied.

The preferred embodiment of the subject invention will now be discussed in conjunction with the figures of the drawings wherein like parts are designated by like reference numerals insofar as it is possible and practical to do so.

Referring first to FIG. 1 of the drawings, a simplified side-view of a body part 10 of a leg to which the device 20 for increasing blood flow, reducing surrounding pressure and decreasing pain, constructed according to the teachings of the present invention, has been applied is shown. The present invention focuses preferably on surrounding the body part 10 with a hollow hypobaric chamber 24. Preferably, the device 20 for increasing blood flow in, reducing pressure around and decreasing pain in the body part 10 comprises a hollow hypobaric chamber 24 sized and shaped for surrounding the body part 10. The hypobaric chamber 24 preferably comprises chamber walls 28 having an inner surface 32, an outer surface 36 adjacent to an ambient atmosphere 34, a perimeter 38 with a first interruption 37 and a second interruption 39, a first and a second pair of proximate endings, 42 and 44 respectively, located next to the first and the second interruptions, 37 and 39, respectively, in the perimeter 38. The first and the second interruptions, 37 and 39, may be most preferably located on two adjacent sides 46 of the chamber 24. Preferably, the first interruption 37 may be located on a first side 47 of the chamber 24 such that an inlet outlet port 48 is created between the first pair of proximate endings 42 on the first side 47. The inlet outlet port 48 may preferably serve as an entry and an exit for the body part 10 under treatment. The second interruption 39 may be most preferably located on a second side 57 of the chamber 24 between a second pair of proximate endings 44. Preferably, the second pair of proximate endings 44 may be located on the second side 57 adjacent to the first side 47 of the chamber 24. The second interruption 39 may most preferably serve as a connection between the chamber 24 and the ambient atmosphere 34.

The device 20 also preferably comprises a means for inhibiting flow of gas 60 in or out of the chamber 24 adjacent to the surface 11 of the body part 10. The means for inhibiting flow of gas 60 most preferably comprises an inflatable seal 62. Preferably, the inflatable seal 62 may be attached to the first pair of proximate endings 42 on the first side 47 of the chamber 24. In a preferred embodiment, the inflatable seal 62 may be located such that when the body part 10 is inserted into the chamber 24 and the seal 62 is inflated, the seal 62 preferably inhibits gas flow in or out of the chamber 24 adjacent to the surface 11 of the body part 10.

Preferably, the device 20 further comprises a means for adjusting pressure 70 in the chamber 24 by withdrawing air from the chamber 24 to create a hypobaric chamber 24. Such means for adjusting pressure 70 preferably comprises a first pipe 72, extending between a pump 76 and the chamber 24, and a first pressure relief valve 78, for adjusting the flow of air between the pump 76 and the chamber 24. Gas may be most preferably withdrawn through the first pipe 72 from the chamber 24 and relieved through adjustments made on the first pressure relief valve 78 into the ambient atmosphere 34.

Furthermore, the device 20 preferably comprises a means for adjusting volume and pressure 80 in the inflatable seal 62. The means for adjusting volume and pressure 80 in the seal 62 most preferably comprises a second pipe 82 extending from the pump 76 to the inflatable seal 62, and a second pressure relief valve 88 for adjusting the flow of gas between the pump 76 and the inflatable seal 62 such that gas may be supplied by the pump 76 to the inflatable seal 62 to an extent that the inflatable seal 62 may preferably fit tightly against the body part 10 and such that gas may be preferably withdrawn from the inflatable seal 62 through adjustments made on the second pressure relief valve 88.

Through the use of such a device 20 the body part 10 of a patient may be preferably positioned within the hollow chamber 24 such that the inflatable seal 62 sealingly contacts the body part 10 in order to form an airtight seal 62 upon being inflated. As required for purposes of treatment, after setting up an airtight seal 62, a hypobaric chamber 24 may be preferably formed by closing the first pressure relief valve 78 and by pumping out gas comprising air from the chamber 24 upon using the means for adjusting pressure 70 in the chamber 24.

The hollow hypobaric chamber 24 in FIG. 1 may be most preferably fabricated from a relatively light material in order to be portable. In addition, the chamber 24 may be preferably fabricated from a transparent material. In a preferred embodiment, the chamber 24 may be most preferably fabricated from plastic materials or plexiglass, if transparency is desired so as to allow observation of the body part 10. In a preferred embodiment, the inflatable seal 62 of the hollow hypobaric chamber 24 may be fabricated from synthetic rubber. It may be seen by those skilled in the art of the invention from the foregoing teachings that other materials than described may work as well. The chamber walls 28 should be preferably shaped to provide maximum strength with reasonably low weight.

In this device 20, the inflatable seal 62 of said hollow hypobaric chamber 24 may be most preferably donut-like in shape when inflated fully. The chamber 24 of the device 20 may be preferably cylindrical in shape. In addition, the chamber 24 may be preferably multi-sided. Preferably, the inflatable seal 62 may be located on and attached to the first pair of proximate endings 42 on the first side 47 of the chamber 24. The means for adjusting pressure 70 in the chamber 24 may be preferably located on and attached to the pair of endings 44 on the second side 57 of the chamber 24 which is adjacent to the first side 47. Preferably, other remaining sides 90 of a chamber 24 which may be multi-sided may comprise uninterrupted chamber walls 92.

The means for adjusting pressure 70 in the chamber 24 by withdrawing gas comprising air from the chamber 24 to make the chamber 24 hypobaric, may preferably comprise at least one interruption 39 for gas outlet. The interruption for gas outlet 39 may most preferably form an obstruction free gas passageway 71 between said chamber 24 and the ambient atmosphere 34 of said chamber 24.

FIG. 1 also preferably presents a method for reducing pressure around the body part 10. Most preferably, the method for reducing such pressure comprises surrounding the body part 10 by the hollow hypobaric chamber 24 sized and shaped for such body part 10. The body part 10 is preferably inserted through the inlet outlet port 48 existing amidst the donut-like inflatable seal 62 which is most preferably attached to the first pair of proximate endings 42 located at the interruption 37 in the perimeter 38 of the hypobaric chamber 24.

Additionally, FIG. 1 preferably presents a method for increasing blood flow associated with diabetes. The method of increasing blood flow most preferably comprises surrounding the body part 10 by the hollow hypobaric chamber 24 sized and shaped for such body part 10. Preferably, the body part 10 is inserted through the inlet outlet port 48 existing amidst the donut-like inflatable seal 62. The inflatable seal 62 may be preferably attached to the first pair of proximate endings 42 located at the interruption 37 in the perimeter 38 of the hypobaric chamber 24.

In addition, preferably, FIG. 1 may present a method for decreasing pain on the body part 10 by reducing pressure around the body part 10. The method for decreasing pain most preferably comprises surrounding the body part 10 by the hollow hypobaric chamber 24 sized and shaped such that the body part 10 is inserted through the inlet outlet port 48 existing amidst the donut-like inflatable seal 62, attached to the first pair of proximate endings 42 located at the interruption 37 in the perimeter 38 of the hypobaric chamber 24.

Figure 2:
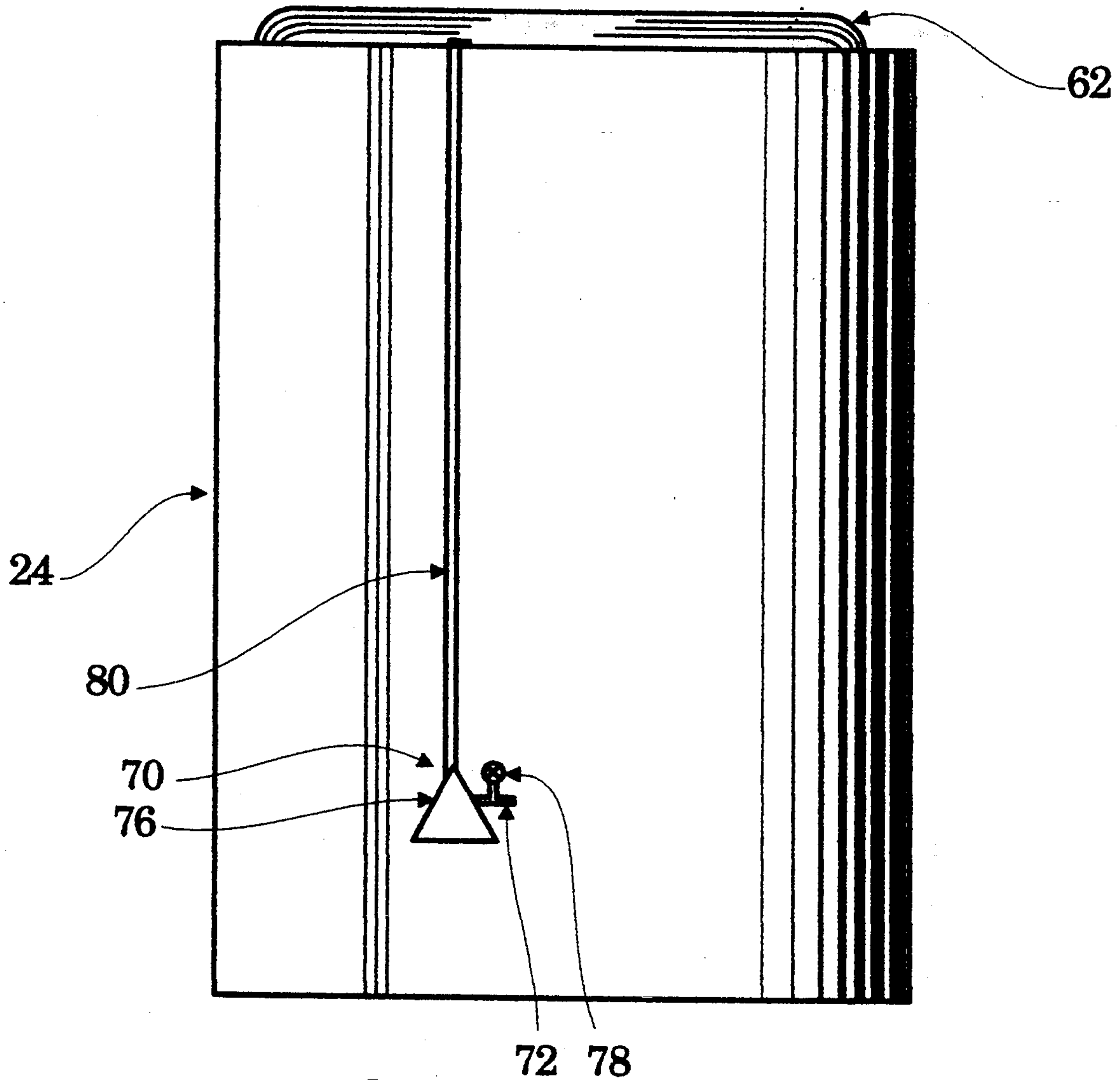
FIG. 2 is a back-view of the device for reducing pressure around the body part, such back view constructed according to the teachings of the present invention.
Figure 3:
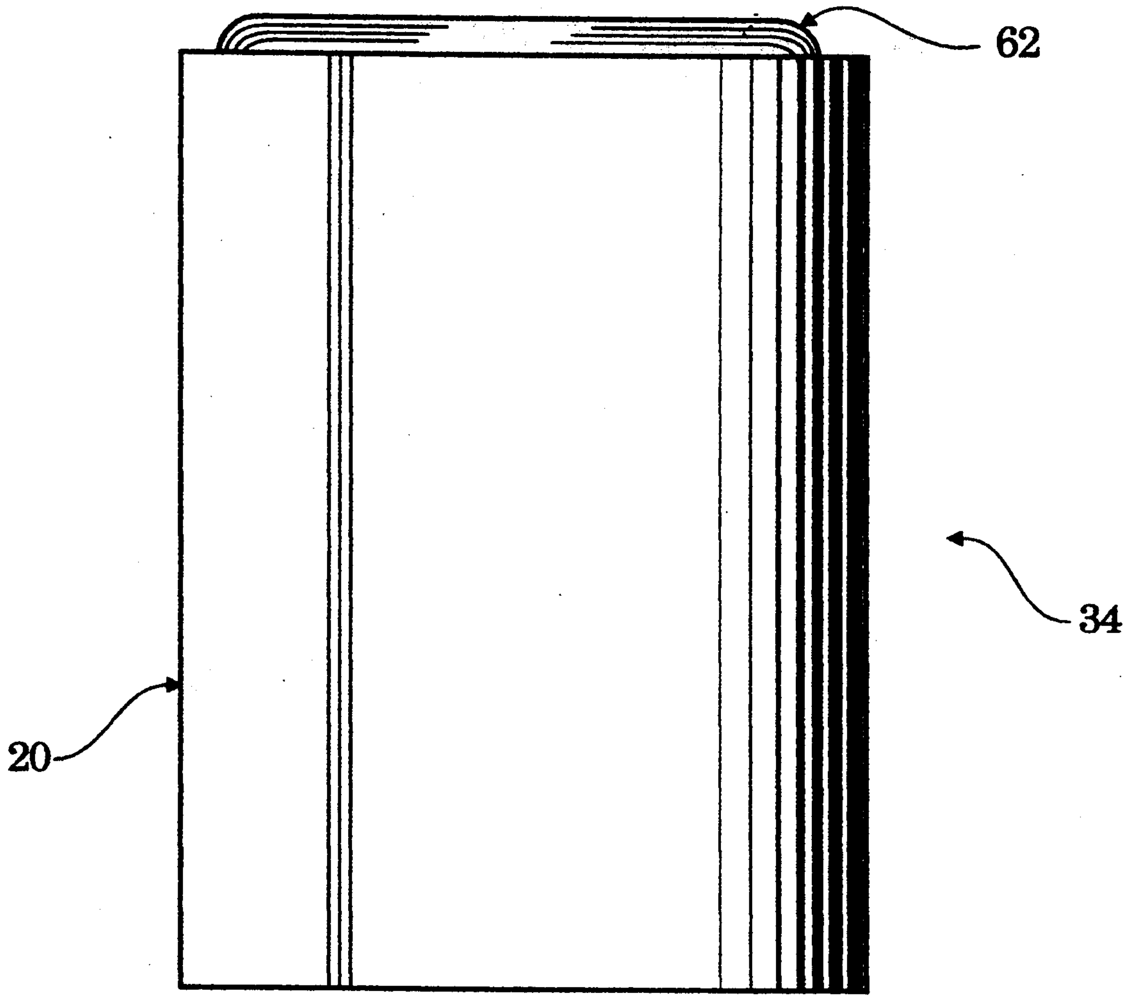
FIG. 3 is a front-view of the device for reducing pressure around the body part, such front-view constructed according to the teachings of the present invention.

FIGS. 2 and 3 represent a back-view and a front-view of the device 20 for reducing pressure around the body part 10. The back-view and the front-view of the device 20 for reducing surrounding pressure are very simple. The front-view is the view of an uninterrupted front view of the chamber 24. The back-view presents a view of the means for adjusting pressure 70 in the chamber 24 and the means for adjusting volume and pressure 80 in the inflatable seal 62.

The operation of the subject invention will now be discussed in conjunction with all of the figures of the drawings. Referring now to FIGS. 1 to 3, the body part 10 may be preferably inserted through the first interruption 37 in the perimeter 38 into the chamber 24. The inflatable seal 62 may be preferably inflated by using the means for adjusting volume and pressure 80 in order to inhibit the flow of gas in or out of the chamber 24 adjacent to the surface 11 of the body part 10. Preferably, at this point the means for adjusting pressure 70 in the chamber 24 may be utilized to withdraw excess gas comprising air and create a hypobaric chamber 24. By adjusting the first and the second pressure relief valves, 78 and 88 respectively, the magnitude of the pressure may be varied to a desired level by an attending physician.

It should be noted that the features of the present invention may be modified to treat different body parts 10 comprising legs and hands. In addition, gases and liquids other than air may be used with the subject invention.

In a preferred embodiment, a pressure of approximately 4 to 5 pounds per square inch may be desired. A lower pressure may also be desirable depending upon individual cases.

From the foregoing, it may readily be seen that the invention comprises a new, unique and useful device which constitutes a considerable improvement over prior art.

Obviously, many modifications and variations of the present invention are possible in light of the above teachings. Therefore, it is to be understood that, within the intended scope of the appended claims, modifications to the invention as described may be made, as might occur to one with skill in the field of the invention. Therefore, all embodiments contemplated have not been shown in complete detail. Other embodiments may be developed without departing from the spirit of the invention or from the scope of the claims.

What is claimed is:

1. A device for reducing pressure around a body part in order to increase blood flow, engorge blood veins and decrease pain in the body part by surrounding the body part in a hollow hypobaric chamber, said device comprising:

(a) the hollow hypobaric chamber sized and shaped for surrounding the body part, said chamber comprising chamber walls having an inner surface, an outer surface adjacent to a surrounding atmosphere, a perimeter with a first and a second interruption, said first and second interruption located on two adjacent sides of the chamber, the first interruption located on a first side of the chamber such that an inlet outlet port is created serving as an entry and an exit for the body part under treatment, and the second interruption located on a second side of the chamber serves as a connection between the chamber and the surrounding atmosphere;

(b) means for inhibiting flow of gas in or out of the chamber adjacent to the surface of the body part, such means for inhibiting flow of gas comprising, a donut shaped inflatable seal attached to the first interruption of the chamber such that when the body part is inserted amidst the chamber and the seal is inflated, the seal inhibits gas flow in or out of the chamber adjacent to the surface of the body part;

(c) means for adjusting pressure in the chamber by withdrawing gas from the chamber to create a hypobaric chamber, such means for adjusting pressure comprising an air pump, a first pipe extending between the pump and the chamber, and a first pressure relief valve for adjusting the flow of gas between the pump and the chamber, such that the pump's vacuum cycle withdraws gas through the first pipe from the chamber and is relieved through adjustments made on the first pressure relief valve into the surrounding atmosphere; and (d) means for adjusting volume and pressure in the inflatable seal comprising a second pipe extending from the pump to the inflatable seal, and a second pressure relief valve for adjusting the flow of gas comprising air between the pump and the inflatable seal, such that gas is supplied by the pump's pressure cycle to the inflatable seal to an extent that the inflatable seal fits tightly against the body part and such that gas is withdrawn from the inflatable seal through adjustments made on the second pressure relief valve;

whereby the body part of a patient is positioned within the hollow chamber such that the inflatable seal sealingly contacts the body part in order to form an airtight seal upon being inflated, and whereby a hypobaric chamber is provided by closing the first pressure relief valve after pumping out gas from the chamber by using the means for adjusting pressure in the chamber to create a hypobaric chamber as required for purposes of treatment.

2. The device of claim 1 wherein the hollow hypobaric chamber is fabricated from a relatively light material in order to be portable.

3. The device of claim 1 wherein the hollow hypobaric chamber is fabricated from transparent materials.

4. The device of claim 1 wherein the hollow hypobaric chamber is fabricated from plastic materials.

5. The device of claim 1 wherein the hollow hypobaric chamber is fabricated from plexiglass.

6. The device of claim 1 wherein the inflatable seal is fabricated from synthetic rubber.

7. The device of claim 1 wherein the inflatable seal of said airtight hollow hypobaric chamber are donut-like in shape when inflated fully.

8. The device of claim 1 wherein the hollow chamber is cylindrical in shape.

9. The device of claim 1 wherein the chamber is multi-sided and wherein the inflatable seal is located on and attached to the pair of endings on the first side of the chamber, the means for adjusting pressure in the chamber is located on and attached to the pair of endings on the second side of the chamber which is adjacent to the first side, and the other remaining sides of a multi-sided chamber comprise chamber walls without any interruptions.

10. The device of claim 1 wherein the means for adjusting pressure in the chamber by withdrawing gas from the hollow chamber to create a hypobaric chamber comprise at least one interruption for gas outlet, the interruption for gas outlet forming an obstruction free gas passageway between the chamber and ambient atmosphere of the chamber.

11. A method for reducing pressure on a body part comprising the steps:

surrounding a body part by a cylindrical hollow hypobaric chamber, inserting the body part through an inlet outlet port amidst a donut-like inflatable seal located at one end of the cylindrical chamber, inflating said inflatable seal by activating an air pumps, simultaneous with inflating said seal evacuating said chamber by use of said air pump, adjusting pressure in said seal and vacuum in said chamber using pressure relief valves located between said pump and said chamber and seal.

* * * * *